United States Patent van Muiden et al.

[11] Patent Number: 5,674,197
[45] Date of Patent: Oct. 7, 1997

[54] CONTROLLED FLEXIBLE CATHETER

[75] Inventors: Johannes Gerardus Maria van Muiden, Peize; Frans Mous, Drachten, both of Netherlands

[73] Assignee: Cordis Corporation, Miami Lakes, Fla.

[21] Appl. No.: 497,677

[22] Filed: Jun. 30, 1995

[30] Foreign Application Priority Data

Jul. 1, 1994 [NL] Netherlands ............ 94.01107

[51] Int. Cl.$^6$ ...................................... A61M 37/00
[52] U.S. Cl. ...................... 604/95; 604/264; 604/282
[58] Field of Search .................. 604/95, 264, 280, 604/281, 282

[56] References Cited

U.S. PATENT DOCUMENTS

| | | |
|---|---|---|
| 4,586,923 | 5/1986 | Gould et al. ............ 604/95 |
| 4,759,748 | 7/1988 | Reed . |
| 4,898,577 | 2/1990 | Badger et al. .......... 604/95 X |
| 4,906,230 | 3/1990 | Maloney . |
| 4,920,980 | 5/1990 | Jackowski ............ 604/95 X |
| 5,168,864 | 12/1992 | Shockey ............ 604/282 X |
| 5,382,234 | 1/1995 | Cornelius et al. ........ 604/282 X |

FOREIGN PATENT DOCUMENTS

| | | |
|---|---|---|
| 0256478 | 2/1988 | European Pat. Off. . |
| 0306010 | 3/1989 | European Pat. Off. . |
| 0488322 | 6/1992 | European Pat. Off. . |
| 630657 | 12/1994 | European Pat. Off. . |
| 9301857 | 2/1993 | WIPO . |

Primary Examiner—Mark Bockelman
Assistant Examiner—N. Kent Gring
Attorney, Agent, or Firm—Dean L. Garner

[57] ABSTRACT

In accordance with the present invention there is provided a catheter having a tubular body with a proximal end, a distal end and at least one lumen extending therethrough. A predetermined length of the distal end of the body has varying bending stiffness in both the circumferential and longitudinal directions of the tubular body. The catheter further includes a pull wire extending through the lumen. The pull wire has a proximal end and a distal end, the distal end of the pull wire is attached to the distal end of the tubular body. Preferably the catheter has at least two strips of material extending longitudinally along the body. The strips of material are offset from each other in both the circumferential and longitudinal directions. These strips of material have a greater bending stiffness than the tubular body so that the distal end of the body has varying bending stiffness in both the circumferential and longitudinal directions.

8 Claims, 2 Drawing Sheets sed to Stevens.
CONTROLLED FLEXIBLE CATHETER

FIELD OF THE INVENTION

The invention relates to catheters having tube-like bodies with a proximal and a distal end, and at least one lumen extending therethrough. The present invention has even further relation to such a catheter which has varying bending stiffness in the circumferential and longitudinal directions at its distal end.

BACKGROUND OF THE INVENTION

Tubular catheters have been found useful to perform a number of medical procedures such as diagnostic heart catheterization, percutaneous transluminal coronary angioplasty, and various endocardial mapping and ablation procedures. Examples of catheters for endocardial mapping and ablation procedures are described in U.S. Pat. No. 5,324,284 issued to Imran on Jun. 28, 1994, which is hereby incorporated herein by reference. Typically catheters are typically extruded from flexible plastic materials. Rotational stiffness is applied to the plastic catheters by sealing a tubular braided wire sheath within the catheter. Such catheters are shown in U.S. Pat. Nos. 3,485,234 and 3,585,707 issued to Stevens.

Selective catheterization of some of the vessels of the human body is often difficult because of the tortuous path the vessels follow. Such procedures often require multiple catheter exchanges to exchange one shape catheter for another. This increases the time it takes to perform the procedure and can result in increased trauma to the patient. Therefore, it is desirable to have one catheter whose tip shape can be changed while it is in the vessel so as to eliminate the need for catheter exchanges.

In the past catheters, such as those shown in PCT application WO 93/01857 published on Feb. 4, 1993, have been used which could bend in one direction at their tip. This is accomplished by having a pull wire running through the length of the lumen and attached to the catheter at the distal end. The distal end of the catheter has a predetermined region of weakness so that when the wire is pulled at its proximal end the catheter bends in the direction of the region of weakness. However, vessels often follow a very complex path with bends and turns in more than one direction. Therefore, there has been a need for a catheter which can bend and curve in two or more directions and in two or three dimensions so as to follow the tortuous path of a vessel. The present invention provides for a catheter which is able to bend in two or more directions and in three dimensions.

SUMMARY OF THE INVENTION

In accordance with the present invention, there is provided a catheter having a tubular body with a proximal end, a distal end and at least one lumen extending therethrough. A predetermined length of the distal end of the body has varying bending stiffness in both the circumferential and longitudinal directions of the tubular body. The catheter further includes a pull wire extending through the lumen. The pull wire has a proximal end and a distal end. The distal end of the pull wire is attached to the distal end of the tubular body.

In accordance with another aspect of the present invention, there is provided such a catheter as described above wherein the predetermined length of the distal end of the tubular body has at least two strips of material extending longitudinally along the body. The strips of material are offset from each other in both the circumferential and longitudinal directions. These strips of material have a different bending stiffness than the tubular body so that the distal end of the body has varying bending stiffness in both the circumferential and longitudinal directions.

In accordance with another aspect of the present invention there is provided a catheter of the type mentioned above wherein strips of material have a greater bending stiffness than the tubular body.

In accordance with another aspect of the present invention, there is provided a catheter of the type mentioned above wherein the distal end of the pull wire is attached to the distal end of the tubular body so as to be centrally located within the lumen.

In accordance with another aspect of the present invention, there is provided a catheter of the type mentioned above wherein the distal end of the tubular body has a cap disposed thereon and the pull wire is attached to the cap.

BRIEF DESCRIPTION OF THE DRAWINGS

While the specification concludes with claims which particularly point out and distinctly claim the subject matter forming the present invention, it is believed that the invention will be better understood from the following description of the preferred embodiment taken in conjunction with the accompanying drawings in which like reference numerals identify identical elements and wherein:

DETAILED DESCRIPTION OF THE INVENTION

Figure 1:
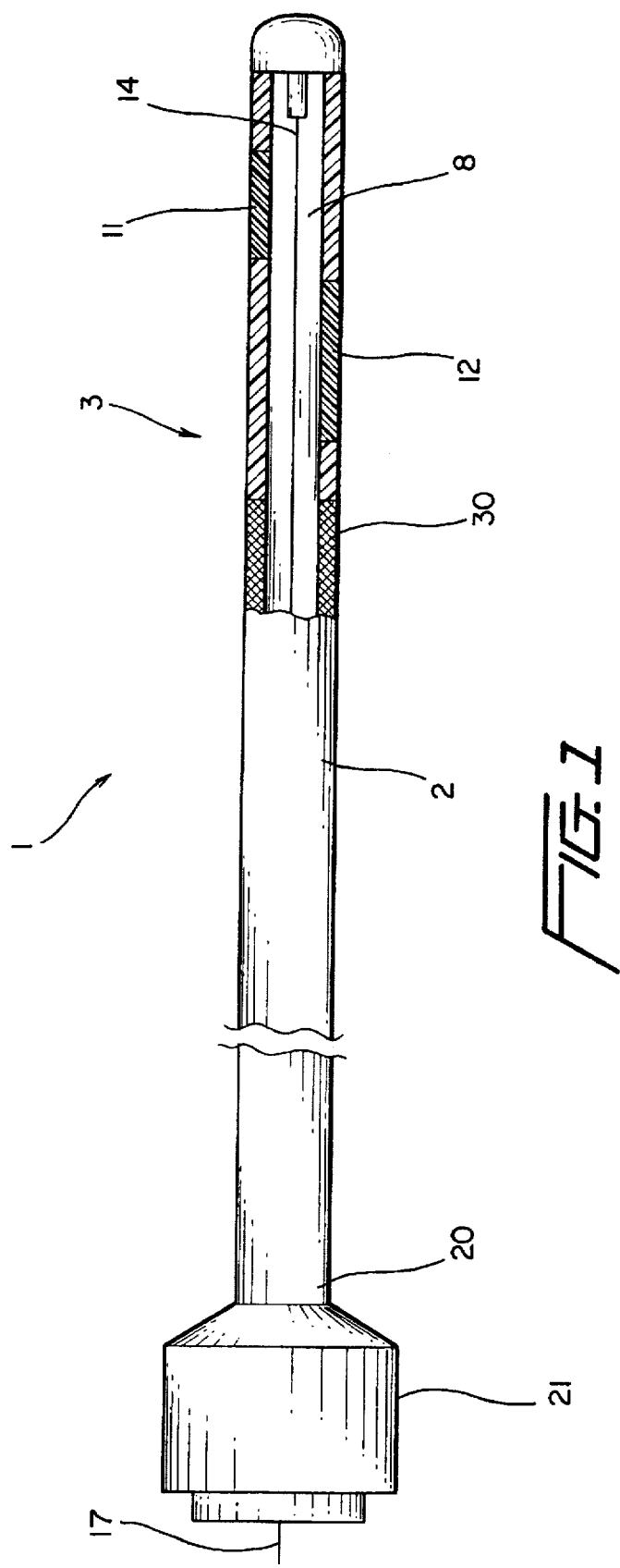
FIG. 1 is a plan view of a catheter in accordance with the present invention having a section cut away at its distal end.

The present invention can best be described by referring to FIG. 1, which shows catheter 1, which can be an angiographic or electrophysiology catheter. Catheter 1 comprises a tube-like basic body 2 having a proximal end 20 attached to a hub 21. The tubular body 2 further includes a distal end 3 and a lumen 8 extending therethrough. Body 2 is shown as being formed from braided wire 30, surrounded by any suitable plastic material. This is to give the catheter stiffness, however, it could be constructed entirely of any suitable plastic material. Construction of such catheters are described in U.S. Pat. No. 3,485,234 issued to Stevens on Dec. 20, 1969 and U.S. Pat. No. 3,585,707 also issued to Stevens on Jun. 22, 1971, both of which are hereby incorporated herein by reference. As seen from the figures, the wire braiding 30 does not extend into the distal most portion of the body 2.

Catheter 1 has a pull wire 4 extending through the lumen. Pull wire 4 has a proximal end 17 and a distal end 14, wherein the distal end 14 of pull wire 4 is attached to the distal end 3 of body 2. The proximal end of the catheter is typically provided with connecting members and a control means for pull wire 4 (not shown). As seen from FIG. 2, pull wire 4 has been attached to catheter 1 by having its distal end attached to a stepped cap 5 which is disposed on the distal end 3 of body 2. Cap 5 includes a shoulder 6 which is placed against the end of a surface 7. The pull wire can be secured to the end cap and the end cap can, during a later stage of the manufacturing process, be fixed to the distal end of the body. The cap is provided with a rounded tip so that on introduction of the catheter into the body, trauma will be reduced. Cap 5 can be made from metal, or molded from any suitable plastic material.

In accordance with the present invention, a predetermined length of distal end 3 of body 2 has varying bending stiffness in both the circumferential and longitudinal direction. This varying bending stiffness in the circumferential and longitudinal directions can be achieved in various ways. One preferred method for achieving this can best be described by referring to FIG. 1 in conjunction with FIG. 2. As shown therein, the predetermined length of distal end 3 which has the varying bending stiffness, comprises two strips of material 11 and 12 extending longitudinally along the tubular body 2. The bending stiffness of strips 11 and 12 is different from that of body 2. Preferably, strips 11 and 12 have a greater bending stiffness than that of the tubular body 2. Manufacture of the predetermined length of the distal end 3 of tubular body 2 with strips 11 and 12 can be accomplished by co-extrusion. The predetermined length of the distal end can be formed integrally with the body or separately formed fused onto it later in the manufacturing process by any suitable means known in the art. The tubular body and the strips can be made from any number of polymers such as polyurethane, polyethylene, etc. The strips can be made from these materials and have a shore hardness of 55 to 75 Durometer. The tubular material can be made from the same materials and having a shore hardness of 40 to 55 Durometer.

Figure 2:
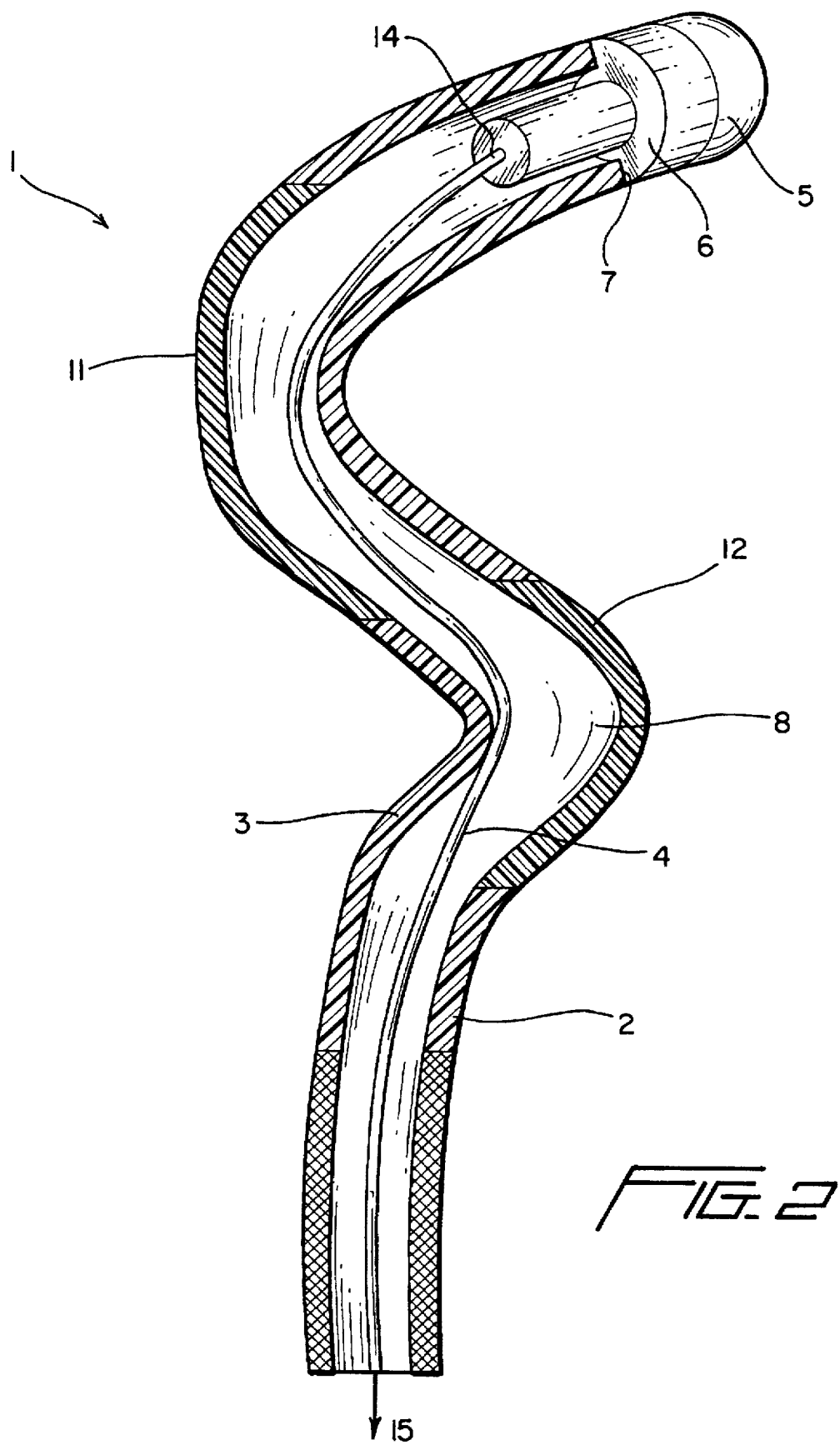
FIG. 2 is a cross-sectional view of the distal end of the catheter wherein tension has been applied to the pull wire.

As shown in FIG. 2, when pull wire 4 is pulled at its proximal end in direction 15 and the strip 11 has a greater bending stiffness than tubular body 2, the distal end 3 will preferably bend and curve in such a direction that strip 11 will be deformed minimally and the portion opposite strip 11 will deform the most since the catheter will want to bend along the path of least resistance. That is, strip 11 will be positioned on the outside of the curve when the distal end 3 is bent. When applying a tensile force in the direction of arrow 15 on the pull wire 4, the distal end 3 will begin bend in the direction shown in FIG. 1. The catheter will always bend in the shape for which the minimum amount of energy is required.

As the wire is pulled it should also start to bend opposite of strip 12 in a similar manner as described above, but at a point proximal to the bend opposite to that of strip 11 since the strips 11 and 12 are offset from each other in the longitudinal direction. Moreover, because strips 11 and 12 are offset from each other in the circumferential direction, when strip 12 is located on the opposite side of the body, an S-bend will be formed when applying a tensile force to the pull wire 4. This is clearly shown in FIG. 2. In addition to such two-dimensional curves it is also possible to allow for three-dimensional bending performance by means of a suitable distribution of strips in various circumferential and longitudinal directions along the body. By doing this the bending performance of the catheter is, so to speak, "preprogrammed". Instead of using two strips, the catheter could have one strip whose length is not parallel to the longitudinal axis of the catheter, but rather curves along a helical line or the like, thereby varying the stiffness of the catheter in both the circumferential and longitudinal directions.

The catheter of the present invention can be manufactured by any number of means known the art including co-extrusion of different materials through a rotating extrusion head on the extrusion machine. By rotating the extrusion head, the desired distribution of the strips in the circumferential and longitudinal direction of the catheter will be achieved.

Although particular embodiments of the present invention have been shown and described, modification may be made to the catheter without departing from the spirit and scope of the present invention. The terms used in describing the invention are used in their descriptive sense and not as terms of limitations.

What is claimed is:

1. A catheter comprising:

(a) a tubular body, made from a first material, having a proximal end, a distal end and at least one lumen extending therethrough said distal end of said body comprising at least two strips within said body, said strips formed of a material which has a different bending stiffness than said first material, said strips separated from each other in both the axial and longitudinal directions, whereby said body has varying bending stiffness in both the circumferential and longitudinal directions; and (b) a pull wire extending through said lumen, said pull wire having a proximal end and a distal end, said distal end of said pull wire is attached to said distal end of said tubular body so that when said proximal end of said pull wire is pulled, said catheter can bend in two separate directions.

2. The catheter according to claim 1 wherein said distal end of said pull wire is attached adjacent to said distal end of said tubular body so as to be centrally located within said lumen.

3. The catheter according to claim 1, wherein said distal end of the tubular body has a cap disposed thereon and said pull wire is attached to said cap.

4. A catheter comprising:

(a) a tubular body, made from a first material, said body having a proximal end, a distal end and at least one lumen extending therethrough, said distal end of said body comprising at least two strips within said body, said strips formed of a material which has a different bending stiffness than said first material, said strips separated from each other in both the axial and longitudinal directions, whereby said body said strips have a greater bending stiffness than said first material so that said tubular body has varying bending stiffness in both the circumferential and longitudinal directions; and (b) a pull wire extending through said lumen, said pull wire having a proximal end and a distal end, said distal end of said pull wire is attached to said distal end of said tubular body so that when said proximal end of said pull wire is pulled, said catheter can bend in two separate directions.

5. The catheter according to claim 4 wherein said distal end of said pull wire is attached adjacent to said distal end of said tubular body so as to be centrally located within said lumen.

6. The catheter according to claim 4, wherein the distal end of the tubular body has a cap disposed thereon and said pull wire is attached to said cap.

7. A catheter comprising:

(a) a tubular body made from a first material, said body having a proximal end, a distal end and at least one lumen extending therethrough, said distal end having a cap attached thereto, said distal end of said body comprising at least two strips within said body, said strips formed of a material which has a different bending stiffness than said first material, said strips separated from each other in both the axial and longitudinal directions, whereby said body, said strips of material have a greater bending stiffness than said first material so that said tubular body has varying bending stiffness in both the circumferential and longitudinal directions; and (b) a pull wire extending through said lumen, said pull wire having a proximal end and a distal end, said distal end of said pull wire is attached to said cap so that when said proximal end of said pull wire is pulled, said catheter can bend in two separate directions.

8. The catheter according to claim 7 wherein said distal end of said pull wire is attached adjacent to said distal end of said tubular body so as to be centrally located within said lumen.

* * * * *